United States Patent
Bharat et al.

(10) Patent No.: US 12,121,403 B2
(45) Date of Patent: Oct. 22, 2024

(54) ULTRASOUND INTERFACE UNIT AND METHOD

(71) Applicant: KONINKLIJKE PHILIPS N.V., Eindhoven (NL)

(72) Inventors: Shyam Bharat, Arlington, MA (US); Jonathan Thomas Sutton, Boston, MA (US); Balasundar Iyyavu Raju, North Andover, MA (US); Harald Greiner, Nufringen (DE); Frank Enslin, Deckenpfronn (DE); McKee Dunn Poland, Andover, MA (US); Martha Gail Grewe Wilson, Andover, MA (US); Ivan Salgo, Pelham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 296 days.

(21) Appl. No.: 17/761,287

(22) PCT Filed: Sep. 20, 2020

(86) PCT No.: PCT/EP2020/076205
§ 371 (c)(1),
(2) Date: Mar. 17, 2022

(87) PCT Pub. No.: WO2021/053204
PCT Pub. Date: Mar. 25, 2021

(65) Prior Publication Data
US 2022/0361853 A1    Nov. 17, 2022

Related U.S. Application Data

(60) Provisional application No. 62/903,026, filed on Sep. 20, 2019.

(30) Foreign Application Priority Data

Oct. 7, 2019  (EP) ..................................... 19201669

(51) Int. Cl.
*A61B 8/00*    (2006.01)
*A61B 8/08*    (2006.01)

(52) U.S. Cl.
CPC .............. *A61B 8/56* (2013.01); *A61B 8/4433* (2013.01); *A61B 8/463* (2013.01); *A61B 8/5223* (2013.01);
(Continued)

(58) Field of Classification Search
CPC ......... A61B 8/56; A61B 8/4433; A61B 8/463; A61B 8/5223; A61B 8/54; A61B 8/585;
(Continued)

(56) References Cited

U.S. PATENT DOCUMENTS 6,524,246 B1 * 2/2003 Kelly ..................... A61B 8/085
600/437
6,705,992 B2  3/2004 Gatzke
(Continued)

FOREIGN PATENT DOCUMENTS

EP    3494893 A1    6/2019
EP    3494895 A1    6/2019
(Continued)

OTHER PUBLICATIONS

International Search Report and Written Opinion for PCT/EP2020/076205; Mailing date: Nov. 4, 2020, 8 pages.
(Continued)

*Primary Examiner* — Sanjay Cattungal (57) ABSTRACT

An interface unit (12) for connecting between an ultrasound sensing apparatus (14) and a patient monitor (18) for providing ultrasound monitoring functionality of one or more physiological or anatomical parameters based on processing of ultrasound data. The interface unit includes means for processing acquired ultrasound data to derive measurements of one or more physiological or anatomical parameters and
(Continued)

is configured for outputting said derived measurements to a coupled patient monitor unit, e.g. for display and/or trending by the patient monitor.

17 Claims, 3 Drawing Sheets

(52) U.S. Cl.
CPC ............... *A61B 8/54* (2013.01); *A61B 8/585* (2013.01); *A61B 8/4405* (2013.01); *A61B 8/4427* (2013.01)

(58) Field of Classification Search
CPC ... A61B 8/4405; A61B 8/4427; A61B 5/0205; A61B 8/0883
See application file for complete search history.

(56) References Cited

U.S. PATENT DOCUMENTS

| | | | |
|---|---|---|---|
| 9,852,272 B1* | 12/2017 | Fram | G16H 10/40 |
| 2003/0163045 A1 | 8/2003 | Gatzke | |
| 2004/0249279 A1 | 12/2004 | Maschke | |
| 2005/0251035 A1* | 11/2005 | Wong | A61B 8/00 |
| | | | 600/459 |
| 2007/0016029 A1* | 1/2007 | Donaldson | A61B 8/565 |
| | | | 600/437 |
| 2009/0299182 A1* | 12/2009 | Asafusa | A61B 8/481 |
| | | | 600/458 |
| 2010/0041968 A1 | 2/2010 | Meschisen et al. | |
| 2011/0246129 A1 | 10/2011 | Ishikawa et al. | |
| 2013/0345563 A1* | 12/2013 | Stuebe | A61B 5/316 |
| | | | 600/440 |
| 2015/0245816 A1* | 9/2015 | Poland | A61B 8/14 |
| | | | 600/447 |
| 2016/0007956 A1 | 1/2016 | Mauldin et al. | |
| 2016/0081663 A1* | 3/2016 | Chen | G06T 7/62 |
| | | | 600/407 |
| 2016/0106394 A1* | 4/2016 | Kang | A61B 8/465 |
| | | | 600/437 |
| 2017/0124701 A1* | 5/2017 | Liang | A61B 8/5223 |
| 2018/0188946 A1* | 7/2018 | Jun | G16H 40/63 |

FOREIGN PATENT DOCUMENTS

| | | |
|---|---|---|
| JP | H11309144 A | 11/1999 |
| JP | 2001104305 A | 4/2001 |
| JP | 2006115986 A | 5/2006 |
| JP | 2017093813 A | 6/2017 |
| WO | 2009138902 A1 | 11/2009 |

OTHER PUBLICATIONS

Medvedofsky Diego et al.,Three-dimensional echocardiographic quantification of the left-heart chambers using an automated adaptive analytics algorithm: multicentre validation study. Eur Heart J Cardiovasc Imaging., 2018; 19(1), pp. 47-58.

* cited by examiner

ULTRASOUND INTERFACE UNIT AND METHOD

CROSS-REFERENCE TO PRIOR APPLICATIONS

This application is the U.S. National Phase application under 35 U.S.C. § 371 of International Application No. PCT/EP2020/076205, filed on Sep. 20, 2020, which claims the benefit of U.S. Provisional Patent Application No. 62/903,026 filed on Sep. 20, 2019, and European Patent Application No. 19201669.9, filed on Oct. 7, 2019. These applications are hereby incorporated by reference herein.

FIELD OF THE INVENTION

This application relates to an interface unit for an ultrasound system, in particular for interfacing between an ultrasound sensing apparatus and a patient monitoring system.

BACKGROUND OF THE INVENTION

The use of ultrasound in a monitoring capacity, for monitoring certain clinical parameters of a subject, is growing area of interest. Ultrasound data representative of a subject can be acquired on a continuous basis and processed with one or more algorithms to derive measurements or parameters related to the subject. For example, changing size of an anatomical body (e.g. the left ventricle of the heart) over time can be derived and monitored from ultrasound data, and used to make clinical assessments (e.g. heart function).

When an ultrasound system is used in a monitoring capacity, measurements from generated ultrasound images may be computed from the ultrasound data, and sent to a monitor for graphical trended display, allowing interpretation by a clinical expert. Ultrasound has the potential become a ubiquitous monitoring tool in the care setting.

By way of one example application, the use of transesophageal echocardiography (TEE) for continual monitoring of the heart has been proposed within the medical community. In this context, TEE would be used not only for qualitative viewing of dynamic cardiac motion via traditional ultrasound imaging, but also for making quantitative measurements such as left ventricular (LV) volume, stroke volume (SV), cardiac output (CO) etc. Model-based segmentation (MBS) could be used to assist in this, for example for automatically segmenting one or more cardiac chambers, enabling anatomic quantification. Other methods of quantitative measurement-making are also possible, such as a full MBS performed on an end-diastolic (ED) frame, followed by 2D or 3D tracking of the segmentation boundaries over the other frames of the cardiac cycle.

Transthoracic echocardiography (TTE) is also used for cardiac evaluation in certain settings, more notably in point-of-care and primary care type settings, but also potentially in others.

Patient monitors collect and display information from a variety of sensors in a hospital setting, including but not limited to, heart rate, blood pressure, body temperature, respiration rate, oxygen saturation etc. The monitor is the central hub for accessing any information on vital signs of the patient. Information can be trended over extended periods within the monitor database, or communicated to a higher level picture archiving and communication system (PACS). The monitor may also be configured to sound an alarm in response to evaluation of certain measurements.

The use of ultrasound in a monitoring context places new demands on the functionality of equipment such as ultrasound systems and patient monitors. Measurements have to be computed from ultrasound data (e.g. ultrasound images) and preferably displayed in a meaningful manner for viewing by clinical personnel in the room, without impeding current standard-of-care. For example, measurements (waveforms or numerical data) generated from ultrasound data may need to be ported to and displayed on a patient monitor.

In addition, ultrasound sensing equipment must be controlled so as to acquire ultrasound data on an on-going basis of a format which is suitable for deriving and continuously monitoring the clinical parameters of interest.

These requirements impose new technical demands beyond that provided by current ultrasound sensing and patient monitoring equipment, and as a result dedicated ultrasound monitoring systems are in development to facilitate this. These impose significant cost burdens on hospitals and other care centers and also necessitate additional space requirements in clinical rooms to accommodate the new systems.

Improvements within the field of ultrasound monitoring which can address one or more of these problems would be of advantage.

SUMMARY OF THE INVENTION

The invention is defined by the claims.

According to examples in accordance with an aspect of the invention, there is provided an ultrasound interface unit, communicatively coupleable in use with an ultrasound sensing apparatus and with a patient monitoring unit, the ultrasound interface unit configured in use to:

receive from the ultrasound sensing apparatus acquired ultrasound data representative of a subject, and perform processing of said data to derive at least one physiological or anatomical parameter related to the subject;

generate a data output representative of said derived parameter and communicate said data output to the patient monitoring unit, and perform a configuration function comprising communicating with the ultrasound sensing apparatus to cause adjustment of one or more operating parameters of the ultrasound sensing apparatus for configuring the ultrasound sensing apparatus to acquire ultrasound data suitable for monitoring said physiological or anatomical parameter.

In one advantageous set of embodiments, the interface unit may be further configured to generate guidance information for guiding a user in positioning an ultrasound transducer unit of the ultrasound sensing apparatus relative to the subject for acquiring ultrasound data suitable for determining said at least one physiological or anatomical parameter. The interface unit may be configured to generate a display output for use in controlling a display unit to display said guidance information.

The interface unit effectively provides a universal processor unit which allows any ultrasound sensing apparatus and patient monitor to be utilized to perform ultrasound monitoring. The interface unit includes means for implementing the processing functions required for deriving and monitoring measurements from ultrasound data, and for communicating these to a patient monitor for display and trending. It may also include the means for controlling the ultrasound apparatus to acquire data in a mode, manner or format which is suitable for deriving and monitoring these measurements.

Hence, the interface unit effectively allows any ultrasound and patient monitoring apparatus to be harnessed for ultrasound monitoring. This avoids the need to purchase and implement a dedicated ultrasound monitoring system, thus saving both space and clinical resources. A single set of ultrasound scanning and patient monitoring equipment can be used both for traditional ultrasound scanning and patient monitoring applications, and also for ultrasound monitoring applications when needed.

The interface unit may in examples provide a retrofit functionality, allowing an existing ultrasound apparatus and patient monitor to be utilized for patient monitoring. The interface unit may be a plug-in unit configured to connect to a separate ultrasound sensing apparatus and patient monitoring unit. However, in other examples, the interface unit may for example be integrated within either an ultrasound apparatus or patient monitor unit, to add ultrasound monitoring functionality to these devices.

The interface unit is preferably configured to recurrently receive ultrasound data from the ultrasound sensing apparatus and to recurrently determine values of said at least one physiological or anatomical parameter. In this way, the interface unit may implement monitoring of said at least one physiological or anatomical parameter.

Monitoring in the context of this disclosure means for example monitoring the parameter (e.g. in an ongoing or continuous manner) over a period of time, e.g. recurrently determining values of the parameter, and for example logging said values.

The interface unit may comprise a processing arrangement comprising one or more processors for performing one or more of the above steps.

As mentioned above, the interface unit is arranged to be communicatively coupleable in use with a patient monitoring unit. By way of example, the interface unit may be configured to connect via wired or wireless connection to the patient monitoring unit. It may be configured to connect via institutional wireless LAN in some examples. The interface unit may include a wired or wireless connection port for facilitating this in some examples. The interface unit is configured in use to communicate physiological and/or anatomical parameter measurements derived by the interface unit. These may for example be displayed on the patient monitoring unit screen and/or stored or cached at the patient monitoring unit. They may be trended on the patient monitor's display for example, i.e. showing changes in the parameter over time.

The interface unit is configured to perform a configuration function comprising communicating with the ultrasound sensing apparatus to cause adjustment of one or more operating parameters of the ultrasound sensing apparatus for configuring the ultrasound sensing apparatus to acquire ultrasound data suitable for monitoring said physiological or anatomical parameter. As will be discussed below, there are different ways for implementing this.

In some examples, the ultrasound sensing apparatus may include local means for controlling ultrasound data acquisition in a manner suitable for performing ultrasound monitoring. For instance, it may include one or more local operating settings or modes for operating ultrasound data acquisition in a manner suitable for performing ultrasound monitoring of the at least one physiological or anatomical parameter. In this case, the interface unit may detect this and may permit the ultrasound sensing apparatus to operate in accordance with this local setting or mode.

In some examples, the ultrasound sensing apparatus may not include any dedicated setting or mode for acquiring the suitable data for performing the ultrasound monitoring. In these cases, the interface unit may detect this, and may itself be configured to direct the mode or manner of data acquisition by the ultrasound sensing apparatus such that data is acquired suitable for monitoring the at least one physiological or anatomical parameter.

In some examples, the patient monitoring unit may include one or more pre-configured, or user-configured, settings or modes for receiving and monitoring one or more ultrasound-derived physiological or anatomical parameters. The interface unit may be configured in use to perform the configuration function in accordance with this setting or mode of the patient monitoring unit. For example, the patient monitor may communicate a particular one or more parameters to be derived from the ultrasound data, and the interface unit may cause configuration of the ultrasound operating parameters such as to realize acquisition of ultrasound data suitable for deriving these one or more parameters.

The patient monitoring unit may include a user interface means for receiving input from the user indicative of one or more parameters to be acquired and the interface unit may be configured in use to receive an indication of these one or more parameters from the patient monitoring unit and configure the ultrasound operating parameters accordingly.

The above represent only example operating approaches and many other particular approaches are also possible, as will be explained and outlined in more detail in descriptions to follow.

According to one possible set of embodiments, the ultrasound interface unit may be configured in use to supply power to the ultrasound sensing apparatus for driving ultrasound transmission by ultrasound transducers of the ultrasound sensing apparatus. This allows for example a stand-alone peripheral ultrasound transducer unit (e.g. an ultrasound probe or scanner) to be utilized as the ultrasound apparatus, without the need for an additional power supply to drive the transducer unit. This allows for a very simple and streamlined set-up, since a full diagnostic ultrasound system is not needed; only a single peripheral ultrasound scanner or transducer unit is needed, where this is powered by the ultrasound interface unit.

The ultrasound interface unit hence provides a power source for the ultrasound transducers of the ultrasound sensing apparatus in this case.

By way of example, the ultrasound sensing apparatus may be an ultrasound transducer unit comprising one or more ultrasound transducers.

By way of example, the ultrasound interface unit may be configured to generate drive signals for driving ultrasound transmission by the ultrasound transducers of the ultrasound transducer unit, wherein the configuration function comprises configuring parameters of said drive signals. The drive signals are electrical drive signals which energize the ultrasound transducers according to a desired transmission pattern for acquiring ultrasound data of a suitable format or mode, so as to induce acquisition of the suitable ultrasound data. Thus the drive signals provide the power supply for the ultrasound transducers.

The ultrasound transducer unit is arranged to receive these drive signals from the interface unit. It need comprise no additional power input connection.

The interface unit may be configured to receive RF echo signal data from the ultrasound transducer unit and process the RF echo signal data to obtain one or more ultrasound images.

In this embodiment the ultrasound transducer would not necessarily need to perform beamforming of the acquired RF echo signals, these signals would be directly streamed to the interface unit, wherein an appropriate signal summing/combination would be performed in order to obtain ultrasound images. This might help reducing costs for the transducers, because more expansive signal processing circuitry would not be needed for such transducers.

According to a further set of embodiments, the ultrasound interface unit may be adapted to be communicatively coupleable with an ultrasound sensing apparatus which includes local drive means for generating drive signals for driving ultrasound transmission by transducers of the ultrasound sensing apparatus, and wherein the configuring function comprises communicating with the ultrasound sensing apparatus to cause the ultrasound sensing apparatus to adjust parameters of said locally generated drive signals. For example, the interface unit may be configured to communicate with a control unit of the ultrasound sensing apparatus to cause the ultrasound sensing apparatus to adjust parameters of said locally generated drive signals. The ultrasound sensing apparatus may comprise an ultrasound transducer unit (e.g. an ultrasound probe) and wherein the local drive means of the ultrasound sensing apparatus is for generating drive signals for driving ultrasound transmission by transducers comprised by the transducer unit.

The interface unit may issue control commands for example, for causing a local transmit controller (control unit) of the ultrasound apparatus to adjust ultrasound acquisition parameters (e.g. transmit or receive parameters). The control unit may communicate with the local drive means to cause adjustment of the acquisition parameters.

The interface unit may be adapted to transmit control commands in the form of one or more data signals or data messages to a control unit of the ultrasound sensing apparatus. The control unit of the ultrasound sensing apparatus may communicate with the local drive means to cause adjustment in the ultrasound acquisition parameters (e.g. transmit/receive signals) based on the received data signals or data messages.

Hence in these examples, the interface unit does not directly drive ultrasound transmission by the ultrasound apparatus transducers, but instead communicates with local control means of the ultrasound apparatus to induce the apparatus to adjust the transducer operating parameters, e.g. acquisition parameters. The ultrasound apparatus may in this case comprise an ultrasound system having dedicated local transmit/receive control means.

In accordance with one possible set of embodiments, the interface unit may be selectively operable in each of two modes:
   a first mode in which the interface unit is configured in use to supply power to the ultrasound sensing apparatus for driving ultrasound transmission by ultrasound transducers of the ultrasound sensing apparatus, and
   a second mode in which the ultrasound interface unit is adapted to be communicatively coupleable with an ultrasound sensing apparatus which includes local drive means for generating drive signals for driving ultrasound transmission by transducers of the ultrasound sensing apparatus, and wherein the configuring function comprises communicating with the ultrasound sensing apparatus to cause the ultrasound sensing apparatus to adjust parameters of said locally generated drive signals.

In one or more embodiments, the ultrasound interface unit may further comprise a display unit for displaying the at least one derived anatomical or physiological parameter and/or for displaying one or more ultrasound images generated based on the acquired ultrasound data. This hence provides a secondary display, supplementary to the display of the patient monitor unit, allowing the at least one derived and monitored physiological or anatomical parameter to be displayed directly on this secondary display.

As mentioned above, in accordance with one or more embodiments, the interface unit may be further configured to generate guidance information for guiding a user in positioning an ultrasound transducer unit or sensor of the ultrasound apparatus relative to the subject for acquiring ultrasound data suitable for determining said at least one physiological or anatomical parameter.

The interface unit may be configured to generate an information output comprising said derived information, for output for example to a display unit coupled or coupleable with the interface unit in use, or for output to the patient monitor for example.

The guidance information may for example be information for guiding a user in correct placement of an ultrasound transducer unit or sensor relative to a subject in order to acquire optimum quality ultrasound data for deriving the desired one or more physiological or anatomical parameters. The interface unit may analyze received ultrasound data with one or more algorithms to asses a quality level of the data for deriving the parameters or measurements of interest.

The guidance information may include information for guiding adjustment of a position of the ultrasound transducer unit or sensor relative to the body. The interface unit may generate a display output for controlling a display unit to display guidance information for adjustment of the ultrasound transducer unit or sensor position. This may be graphical or visual guidance information for example.

In one set of examples, the ultrasound sensing apparatus may (further) comprise a display unit and wherein the ultrasound interface unit is adapted to communicate said display output to the ultrasound sensing apparatus for causing display of the guidance information on the display unit of the ultrasound sensing apparatus.

In one set of examples, the ultrasound sensing apparatus may comprise a display unit and wherein the ultrasound interface unit is configured to communicate with the ultrasound sensing apparatus to cause display on said display unit of the at least one physiological or anatomical parameter derived by the interface unit.

The configuration function comprises causing adjustment in one or more operating parameters of the ultrasound sensing apparatus for configuring the ultrasound sensing apparatus to acquire ultrasound data suitable for ultrasound monitoring purposes. The operating parameters may for example include acquisition settings of the ultrasound transducers of the ultrasound sensing apparatus. These may include for example a transmit and/or receive frequency of the transducers, delay timings for transmit and receive by the transducers (e.g. to adjust beamforming settings), a drive voltage of the transducers, and/or a drive pattern for the transducers (e.g. for adjusting beamforming). These may additionally or alternatively include, for example, transmit voltage, line density, beam widths, 2D vs 3D acquisition mode, field of view size, and/or frame rate.

In accordance with one or more embodiments, the ultrasound data received from the ultrasound sensing apparatus may include ultrasound image data. For example, it may comprise one or more ultrasound images.

For example, the ultrasound sensing apparatus may include processing means for processing received data to generate one or more ultrasound images, and wherein the ultrasound data received at the interface unit from the ultrasound sensing apparatus includes image data.

The ultrasound sensing apparatus may, by way of non-limiting example, comprise an ultrasound imaging system comprising one or more ultrasound scanners or transducer units for acquiring ultrasound data, plus one or more processors for at least partially processing the data. These local processors may process the ultrasound data to generate one or more images for example, and/or may perform beamforming, for instance based on a delay sum approach.

In accordance with one or more embodiments, the ultrasound interface unit may be adapted to receive an input signal from the patient monitoring unit and may be adapted to perform the configuring of the operating parameters of the ultrasound sensing apparatus based on the input signal.

Thus, in this set of embodiments, adjustment of the ultrasound acquisition (e.g. imaging) settings can be done based on inputs sourced from the patient monitoring unit. The patient monitoring unit may transmit a feedback signal to the interface unit for example responsive to detecting a change in patient monitoring information (e.g. vital signs) meeting a defined criterion, for example, meeting or passing a pre-defined threshold.

Additionally or alternatively, the interface unit may be further configured to generate guidance information for guiding a user in positioning the ultrasound transducer unit of the ultrasound sensing apparatus relative to the subject for acquiring ultrasound data suitable for determining said at least one physiological or anatomical parameter, and wherein the ultrasound interface unit is adapted to receive an input signal from the patient monitoring unit, and wherein the ultrasound interface unit is adapted to configure the guidance information based on the input signal.

Thus in this set of embodiments, the input signal may additionally or alternatively trigger adjustment by the interface unit of the user guidance. For example, it may cause generation of a guidance output which prompts a user to (re)acquire one or more imaging views for an updated image acquisition. The guidance output may provide guidance for positioning the transducer unit relative to the subject.

In accordance with one or more embodiments, the ultrasound interface unit may be further coupleable in use with one or more medical sensors for measuring one or more physiological parameters and the interface unit configured to receive sensor data from said one or more sensors. The interface unit may for example be configured to use said sensor data in combination with the ultrasound data in deriving said at least one physiological or anatomical parameter.

Additionally or alternatively, in some examples, the interface unit may be configured to receive sensor data and/or physiological parameter data from the patient monitoring unit. For example, the patient monitoring unit collects this data via one or more communicatively coupled sensors and then transfers or communicates the data in use to the interface unit.

The interface unit may for example be configured to use said received sensor or parameter data in combination with the ultrasound data in deriving said at least one physiological or anatomical parameter. The interface unit may in some examples display an indication of the sensor or parameter data received from the patient monitoring unit on the optional display unit, for example along with the parameter data acquired using ultrasound.

In accordance with one or more embodiments, the ultrasound interface unit may be configured to generate a control signal for controlling a display unit to display the at least one derived anatomical or physiological parameter and/or to display one or more ultrasound images generated based on the acquired ultrasound data. In these examples, the interface unit may therefore be configured to control an external or auxiliary display to present the derived parameters and/or generated images, where the display may or may not be part of the interface unit itself. The interface unit may be operatively coupleable in use with an external display unit for example.

The interface unit may include processing means for processing the received ultrasound data to generate one or more ultrasound images.

According to one or more examples, the ultrasound interface unit may be configured to control the display unit to display ultrasound images overlaid with said derived one or more physiological or anatomical parameters.

The ultrasound interface unit in certain aspects may be provided in combination with one or both of an ultrasound sensing apparatus and a patient monitor unit, to provide an ultrasound system. There are different options for provision of an ultrasound system, depending upon which parts are included in the system, and which are external and operatively coupleable to the system.

Examples in accordance with one aspect of the invention provide an ultrasound system, comprising:
  an ultrasound sensing apparatus, and
  an ultrasound interface unit in accordance with in accordance with any example or embodiment outlined above or described below, or in accordance with any claim of this application, communicatively coupled with the ultrasound sensing apparatus.

The system may in certain examples further comprise a patient monitoring unit communicatively coupleable with one or more medical sensors for receiving medical sensor data. Alternatively, the interface unit may be adapted to be coupleable in use with a patient monitoring unit.

In one or more examples, the ultrasound sensing apparatus may comprise a base station, and wherein the ultrasound interface unit is integrated within the base station. For example, the interface unit may be physically located within at least one part of a base station housing. The base station may for example comprise processing means for processing ultrasound data acquired by one or more ultrasound transducers to generate one or more ultrasound images.

The ultrasound sensing apparatus may in some examples be a portable or mobile ultrasound sensing apparatus.

The ultrasound sensing apparatus may in certain examples comprise an diagnostic ultrasound system or unit, for instance a trolley-type ultrasound unit comprising an ultrasound transducer unit, processing means, a display and a user input device (e.g. a keyboard and/or pointer device).

Examples in accordance with a further aspect of the invention provide an ultrasound system, comprising:
  a patient monitoring unit being communicatively coupleable with one or more medical sensors for receiving medical sensor data, and
  an ultrasound interface unit in accordance with any example or embodiment outlined above or described below, or in accordance with any claim of this application, communicatively coupled with the patient monitoring unit.

The system may in certain examples further comprise an ultrasound sensing apparatus. Alternatively, the interface unit may be adapted to be coupleable in use with an ultrasound sensing apparatus. The ultrasound sensing apparatus in either case may in certain examples be in accordance with any of the examples discussed above.

In one or more examples, the patient monitoring unit may comprise a base station, and wherein the ultrasound interface unit is integrated within said base station, for example physically located within at least a part of a housing of such a base station. The base station may in examples comprise processing means arranged to receive the medical sensor data.

Examples in accordance with a further aspect of the invention provide an ultrasound interface method, comprising:

receiving from an ultrasound sensing apparatus acquired ultrasound data representative of a subject, and performing processing of said data to derive at least one physiological or anatomical parameter related to the subject;

generating a data output representative of said derived parameter and communicating said data output to a patient monitoring unit, and performing a configuration function comprising communicating with the ultrasound sensing apparatus to cause adjustment of one or more operating parameters of the ultrasound sensing apparatus for configuring the ultrasound sensing apparatus to acquire ultrasound data suitable for monitoring said physiological or anatomical parameter.

According to one or more embodiments, the method may further comprise generating guidance information for guiding a user in positioning an ultrasound transducer unit of the ultrasound sensing apparatus relative to the subject for acquiring ultrasound data suitable for determining said at least one physiological or anatomical parameter; and generating a display output for use in controlling a display unit to display said guidance information for adjustment of the ultrasound transducer unit position.

Examples in accordance with a further aspect of the invention provide a computer program product comprising code means configured, when run on a processor, to cause the processor to perform the interface method in accordance with any example outlined above or described below or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an interface unit for connecting between an ultrasound sensing apparatus and a patient monitor for providing ultrasound monitoring functionality of one or more physiological or anatomical parameters based on processing of ultrasound data. The interface unit includes means for processing acquired ultrasound data to derive measurements of one or more physiological or anatomical parameters and is configured for outputting said derived measurements to a coupled patient monitor unit, e.g. for display and/or trending by the patient monitor.

The interface unit may further include functionality to assist in configuration or set-up of the ultrasound sensing apparatus for use in monitoring the desired one or more physiological or anatomical parameters. This may include for instance means for communicating with the ultrasound sensing apparatus to cause adjustment in one or more operating parameters of the apparatus. This may further include for instance means for generating user guidance information for guiding a user in correct placement of an ultrasound transducer unit or sensor relative to a subject in order to acquire optimum quality ultrasound data for deriving the desired one or more physiological or anatomical parameters. This guidance information may include information for guiding adjustment of a position of the ultrasound transducer unit or sensor relative to the body. The interface unit may generate a display output for displaying on a display unit guidance information for adjustment of the ultrasound transducer unit or sensor position.

Figure 1:
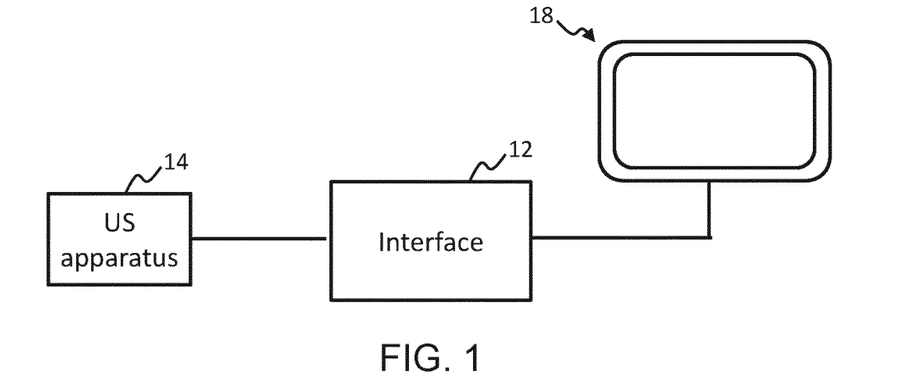
FIG. 1 schematically shows an example ultrasound interface unit in use.

FIG. 1 schematically illustrates an example ultrasound interface unit in accordance with one or more embodiments. The interface unit 12 is shown in use, coupled with an ultrasound sensing apparatus 14 and with a patient monitoring unit 18. Each of these components is illustrated in schematic form only, to show the connection arrangement with respect to the interface unit 12.

The ultrasound sensing apparatus 14 may, by way of non-limiting example, comprise an ultrasound imaging system comprising one or more ultrasound scanners or transducer units for acquiring ultrasound data, plus one or more processors for at least partially processing the data. These local processors may process the ultrasound data to generate one or more images for example, and/or may perform receive beam-forming, for instance based on a delay sum approach. In other examples, the ultrasound sensing apparatus may comprise simply a standalone ultrasound sensor or ultrasound transducer unit comprising one or more transducers.

The patient monitoring unit 18 may by way of example configured to be communicatively coupleable in use with one or more clinical or medical sensors for receiving medical sensor data from the sensors. By way of non-limiting example, such sensors may include a pulse rate sensor (e.g. PPG sensor), a blood pressure sensor, a respiration sensor, a blood oxygen saturation sensor, and/or a body temperature sensor. The patient monitoring unit 18 may include a local display unit for displaying results of the medical sensor data, for instance it may show trended values of the medical sensors over time, e.g. in the form of graphs showing progress of the medical parameters measured by the sensors. It may include user input means for configuring settings of the patient monitor. It may be configured to receive and display sensor data pertaining to a single subject or patient or to multiple subjects and patients.

The ultrasound interface unit 12 is configured to receive from the ultrasound sensing apparatus 14 acquired ultrasound data representative of a subject.

The acquired ultrasound data which is transferred to the interface unit 12 may be 'raw' RF ultrasound data, or it may be data which has been at least partially post-processed. As the skilled person will be aware, within the field of ultrasound diagnostic imaging, acquired RF ultrasound data may be put through a series of processing steps to combine received RF signals, format and configure the data, and then subsequently to derive information from the data such as one or more images, or anatomical or physiological measurements or quantifications. These steps may include any one or more of: beam-summing received signal channels, band-pass filtering, decimation, I and Q component separation, and/or harmonic signal separation, which acts to separate linear and nonlinear signals so as to enable the identification of nonlinear (higher harmonics of the fundamental frequency) echo signals returned from tissue and microbubbles. The steps may also include additional signal enhancement such as speckle reduction, signal compounding, and/or noise elimination. Subsequent to this, the steps can include scan-conversion for converting the acquired ultrasound data into visual image data.

The ultrasound data received by the interface unit may be data at any point along such a series of processing steps.

The ultrasound interface 12 is configured to perform processing of said received ultrasound data to derive at least one physiological or anatomical parameter related to the subject.

The ultrasound interface 12 is further configured to generate a data output representative of said derived at least one parameter and communicate said data output to the patient monitoring unit 18

The ultrasound interface unit 12 is preferably further configured to perform a configuration function comprising communicating with the ultrasound sensing apparatus 14 to cause adjustment of one or more operating parameters of the ultrasound sensing apparatus for configuring the ultrasound sensing apparatus to acquire ultrasound data suitable for monitoring said physiological or anatomical parameter over time.

The operating parameters may for example include acquisition settings of the ultrasound transducers of the ultrasound sensing apparatus. These may include for example a transmit and/or receive frequency of the transducers, delay timings for transmit and receive by the transducers (e.g. to adjust beamforming settings), a drive voltage of the transducers, and/or a drive pattern for the transducers (e.g. for adjusting beamforming). These may additionally or alternatively include, for example, transmit voltage, line density, beam widths, 2D vs 3D acquisition mode, field of view size, and/or frame rate.

The interface unit 12 may include a memory in which a preferred set of one or more operating parameters for the ultrasound sensing apparatus are stored, and wherein the interface unit is configured to retrieve and apply said settings to the ultrasound sensing apparatus 14 in use. Different sets of settings may be stored corresponding to different physiological or anatomical parameters to be derived. The preferred set(s) of one or more settings may alternatively be stored remote from the interface unit, and the interface unit is configured to communicate with for instance a remote server, e.g. via an Internet or network connection, to retrieve the settings.

This configuration function allows the interface unit to be used with any ultrasound sensing or imaging unit, by configuring settings of the ultrasound acquisition function to ensure that the collected ultrasound data is optimal for deriving said at least one physiological or anatomical parameter.

The interface unit 12 may comprise one or more processors for performing any one or more of the above-outlined functions.

In advantageous examples, the interface unit 12 may further comprise a display unit 24 operatively coupled to the interface unit. An example of such an embodiment is shown schematically in FIG. 2. The interface unit may be configured to control the display unit to display the results of the at least one derived anatomical or physiological parameter. The display unit may additionally or alternatively be used to display one or more ultrasound images derived from acquired ultrasound data. Such images may be derived by the interface unit 12 or by suitable processing means of the ultrasound sensing apparatus 14 in examples.

Figure 2:
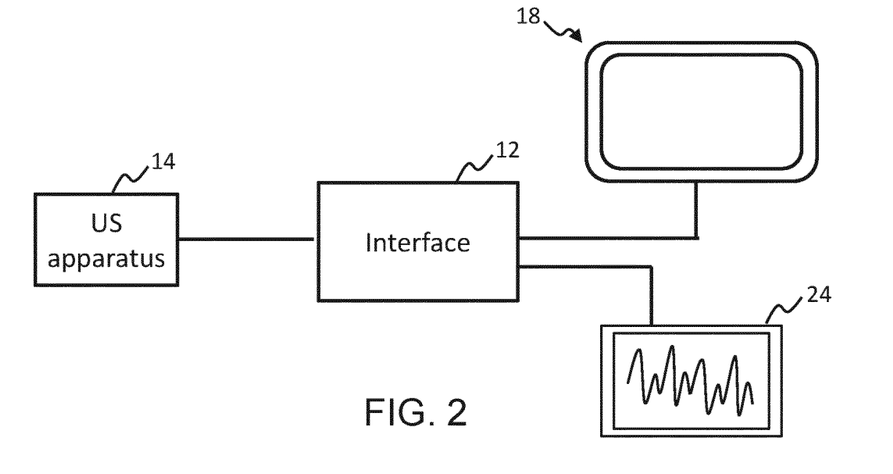
FIG. 2 schematically shows a further example ultrasound interface unit in use.

In some examples, the interface unit 12 may be configured to display on the display unit 24 the results of the derived one or more physiological parameters as an overlay on generated ultrasound images or volumes. By way of example, where the ultrasound data received by the interface unit comprises image data, the results of the one or more parameter quantifications might be depicted overlaid atop, or adjacent to, the ultrasound image used to derive the measurement.

As discussed, the ultrasound interface unit 12 is configured to process received ultrasound data to acquire one or more physiological or anatomical parameters related to the subject. This process may be otherwise referred to as measurement quantification in this disclosure.

Using ultrasound data to derive physiological or anatomical parameter measurements is a known concept. By way of one example, example approaches for processing ultrasound data to extract such measurements are outlined in: Diego Medvedofsky et al, Three-dimensional echocardiographic quantification of the left-heart chambers using an automated adaptive analytics algorithm: multicentre validation study, European Heart Journal-Cardiovascular Imaging, Volume 19, Issue 1, January 2018, Pages 47-58.

By way of non-limiting example, physiological or anatomical parameters which may in examples be derived by the interface unit from the ultrasound data may include one or more of: left/right ventricle volume or outer dimensions, blood flow through one or more blood vessels, heart rate, breathing rate, maximum lung capacity, stroke volume, and cardiac output. Other parameters which may be monitored include the positions and/or shapes of any one or more of: the mitral valve, the tricuspid valve, the atrial and/or ventricular septa wall, and left and/or right atria. The interface unit may perform by way of example any of: mitral valve and/or tricuspid valve tracking and/or segmentations, atrial and/or ventricular septa wall tracking and/or analysis, and left and/or right atrial segmentations.

The acquired ultrasound data may be representative of a particular anatomical region of the subject. This data can then be processed to extract quantitative measurements related to one or more anatomical entities in that region. For example, one or more frames of ultrasound data may be received representative of the heart region at one or more corresponding time points. This can be processed to determine an outer dimension of clinically relevant sections of the heart, such as the left ventricle, at different time points. If frames are captured extending over the course of one or more entire heart cycles, a measure of cardiac output of the patient may be derived for instance.

Processing of the ultrasound data to derive the one or more physiological or anatomical parameters can be performed in some examples using one or more suitable algorithms. These may for example include one or more machine learning algorithms. A machine learning algorithm may be trained with training data comprising various example frames or sets of frames of ultrasound data, and these being labelled with a correct corresponding measure of a physiological or anatomical parameter or measurement of interest.

In other examples, segmentation may be performed on received ultrasound data for deriving the at least one physiological or anatomical parameter. For instance, the received ultrasound data may be ultrasound image data, and a segmentation algorithm applied to this data to extract dimensions of one or more anatomical bodies or entities represented within the data. In advantageous examples, model based segmentation may be applied for instance.

Ultrasound data may be acquired by the ultrasound sensing apparatus 14 on an ongoing or continuous or recurrent basis and received at the ultrasound interface unit 12 in real time in certain examples. The interface unit may process this data (for example also in real-time), allowing recurrent or continuous measurements of the one or more physiological or anatomical parameters to be derived over time. Thus, monitoring of the one or more physiological or anatomical parameters is achieved.

More generally, depending upon the measurement to be derived, the received ultrasound data can be processed in different ways. By way of example, and as explained above, in some cases, AI and model-based segmentation may be applied to received data to extract and measure certain anatomical or physiological parameters (anatomy segmentation). In some examples, blood flow patterns may additionally or alternatively be quantified. In this case, color flow analysis may, by way of example, be performed to derive flow velocities and optionally also spatial variance of these velocities.

According to some examples, means may additionally be provided for enabling a user to make a manual measurement of a particular anatomical or physiological feature (e.g. a valve or chamber wall), e.g. by means of an on-screen caliper or other measurement tool. The system may in some examples comprise means for propagating this measurement temporally over future image frames.

In advantageous examples, the interface unit 12 may be further configured to generate guidance information for guiding a user in positioning an ultrasound transducer unit or sensor of the ultrasound apparatus relative to the subject for acquiring ultrasound data suitable for determining said at least one physiological or anatomical parameter. Thus a smart probe positioning functionality may be implemented.

The guidance information may for example be information for guiding a user in correct placement of an ultrasound transducer unit or sensor relative to a subject in order to acquire optimum quality ultrasound data for deriving the desired one or more physiological or anatomical parameters. The interface unit may analyze received ultrasound data with one or more algorithms to asses a quality level of the data for deriving the parameters or measurements of interest.

The guidance information may include information for guiding adjustment of a position of the ultrasound transducer unit or sensor relative to the body. The interface unit may generate a display output for controlling a display unit to display guidance information for adjustment of the ultrasound transducer unit or sensor position. This may be graphical or visual guidance information for example.

For example, the interface unit may be configured to analyze the received ultrasound data and determine user feedback or guidance for positioning the ultrasound probe in an acceptable position to ensure sufficient quality of the derived at least one physiological or anatomical parameter. For example, the user may manipulate an ultrasound probe, and wherein the interface unit provides, e.g. via a coupled display unit, feedback in real-time on a quality metric or measure of the current ultrasound image. Alternately, the system can actively guide the user to manipulate the probe position/pose in a certain manner to achieve the right view. This may be based for instance on a particular detected viewpoint captured within the data.

For instance, if the parameter to be derived is related to the heart left ventricle, the interface unit may process the received ultrasound data with one or more algorithms configured to detect whether the left ventricle is located within the ultrasound viewpoint, and if it is, whether it is optimally centered within the viewpoint. If not, guidance information may be generated related to how the ultrasound sensor or transducer unit should be moved to capture data with a viewpoint which better represents the anatomical body of interest (e.g. the left ventricle).

Generating of the guidance information may by way of example be implemented using image analysis and/or machine learning algorithms or techniques.

In accordance with one or more examples, the interface unit may include one or more pre-stored algorithms or computer programs (for instance stored on a local memory), adapted to process received ultrasound data and to generate guidance information for guiding the user based on the processing, In some examples, there may be a different algorithm or program stored for each of the possible one or more anatomical or physiological parameters to be derived. In some examples, the interface unit may be adapted to establish a communication channel with a remote server storing one or more algorithms or programs for processing ultrasound data and generating output guidance information, and adapted to retrieve at least one of the algorithms or programs for use in generating the guidance information.

In some examples, the ultrasound interface unit may be configured to receive positioning data representative of relative or absolute position or motion of an ultrasound sensor or transducer unit comprised by the ultrasound sensing apparatus 14. The ultrasound apparatus 14 may for example comprise one or more motion sensors incorporated within the ultrasound sensor or ultrasound transducer unit of the apparatus for detecting movement and/or position of this sensor or transducer unit. This movement and/or position data may be communicated in real-time to the ultrasound interface unit 12 in certain examples to use in conjunction with ultrasound and/or vital signs data for use in deriving said user guidance information and/or ultrasound signal quality metrics.

As mentioned above, the interface unit may be adapted to generate a display output for controlling a display unit to display the guidance information. In one set of advantageous examples, the ultrasound sensing apparatus may further comprise a display unit and wherein the ultrasound interface unit is adapted to communicate said display output to the ultrasound sensing apparatus for causing display of the guidance information on the display unit of the ultrasound sensing apparatus. Alternatively, the interface unit may comprise a local display unit and wherein the display output is communicated to said local display unit.

In accordance with one or more embodiments, the ultrasound interface unit may be adapted to receive an input signal from the patient monitoring unit and may be adapted to perform the configuring of the operating parameters of the ultrasound sensing apparatus based on the input signal.

Thus, in this set of embodiments, adjustment of the ultrasound acquisition (e.g. imaging) settings can be done based on inputs sourced from the patient monitoring unit. The patient monitoring may transmit a feedback signal to the interface unit, for example responsive to detecting a change in patient monitoring information (e.g. vital signs) meeting a defined criterion, for example, meeting or passing a pre-defined threshold.

Additionally or alternatively, the interface unit may be further configured to generate guidance information for guiding a user in positioning the ultrasound transducer unit of the ultrasound sensing apparatus relative to the subject for acquiring ultrasound data suitable for determining said at least one physiological or anatomical parameter, and wherein the ultrasound interface unit is adapted to receive an input signal from the patient monitoring unit, and wherein the ultrasound interface unit is adapted to configure the guidance information based on the input signal.

Thus in this set of embodiments, the input signal may additionally or alternatively trigger adjustment by the interface unit of the user guidance. For example, it may cause generation of a guidance output which prompts a user to (re)acquire one or more imaging views for an updated image acquisition. The guidance output may provide guidance for positioning the transducer unit relative to the subject.

A benefit of this embodiment is that it allows generation of a snapshot of the relevant anatomy (e.g. cardiac) close to a detected time of a change in the one or more physiological parameters, allowing a clinician to derive an improved understanding of a cause of the change.

In advantageous embodiments, the ultrasound interface unit may be further configured to receive non-ultrasound-based medical sensor data, e.g. subject vital sign data, and to use this data in determining the one or more physiological or anatomical parameters.

For example, the ultrasound interface unit may be further coupleable in use with one or more medical sensors for measuring one or more physiological parameters and wherein the interface unit is configured to receive sensor data from said one or more sensors. Alternatively, the interface unit may receive medical sensor data via the patient monitoring unit 18, the patient monitoring unit being operatively coupled with one or more medical sensors for receiving this medical sensor data.

The one or more physiological parameters measured by the medical sensors may, by way of non-limiting example, include patient vital signs such as pulse rate, respiration rate, body temperature, blood pressure and/or blood oxygen saturation (SpO2).

By way of example, vital signs data or other medical sensor data that are acquired and displayed on the patient monitoring unit 18 can be sampled by the ultrasound interface unit 12 and used in deriving the one or more physiological or anatomical parameters.

Medical sensor data may also be used to facilitate additional or alternative functionality. For example, it may be used as a basis for triggering acquisition of ultrasound data in some examples. For instance, acquisition of ultrasound data and deriving of the at least one physiological or anatomical parameter from that data may be triggered only in response to a certain threshold level of one or more parameters monitored by a medical sensor being reached or exceeded. For instance, measuring cardiac output might only be triggered responsive to measuring a fall or rise in pulse rate by a certain amount or to a certain absolute level.

In cases in which the ultrasound interface unit 12 includes a coupled display unit 24, the interface unit may be configured to display received medical sensor data on said display, whether this is received from auxiliary medical sensors coupled to the interface unit 12 or received via the patient monitoring unit 18.

By way of example, waveforms and/or numerical medical sensor data from the patient monitoring unit 18 may be replicated for display on the interface unit 12 display 24. In some examples, the interface unit may for instance serve as a useful additional portable device (e.g., clinician's handheld or mobile device) where patient monitor information can be accessed.

According to one or more examples, a given patient monitoring unit 18 may be paired with a given ultrasound interface unit 12 such that the two are communicably coupled to another. In some examples, there may be provided near field communication means within the interface unit 12 for facilitating such pairing. For example, pairing with a given patient monitoring unit may be triggered responsive to tapping/touching on the patient monitor, e.g. the patient monitor screen, using for example Near Field Communication (NFC) tags. If the patient monitor is stationary and difficult to reach (e.g. mounted high on a wall), a surrogate NFC assignment via a different device is possible, e.g. with a peripheral pairing touch pad of the patient monitor located closer to the ground and communicatively coupled with the patient monitor 18.

In accordance with one or more embodiments, the ultrasound interface unit 12 may include a user input means for receiving user input commands. The interface unit may be configured to adjust or configure one or more operating settings based on received user input. By way of example, the interface unit may be configured to utilize user input commands in performing said configuration function for configuring the operating parameters of the ultrasound sensing apparatus. For example, the interface unit may permit entry via the user input means of preferred operating parameter settings for the ultrasound sensing apparatus 14 and may configure the ultrasound sensing apparatus accordingly. The operating parameters may include, by way of example, acquisition interval, scanning location (e.g. a target location for beam-form steering), scanning frequency. In the absence of user input, the interface unit may instead automatically determine operating parameters for the ultrasound sensing apparatus, for instance based on stored defaults, as discussed above.

User input may also be used to set the at least one physiological or anatomical parameters to be derived by the interface unit based on the received ultrasound data.

The ultrasound interface unit 12 may be operable to derive from received ultrasound data any one or more of a range of different physiological or anatomical parameters. The ultrasound interface unit may be adapted to configure which parameters are derived from acquired data based on received user input in some examples. In other examples, it may be determined automatically, e.g. based on data from other medical sensors (as discussed above), or based on time of day, or for instance based on patient history.

In accordance with one or more examples, the ultrasound interface unit may include communication means for communicating with a further computer or system for exporting derived values of the at least one physiological or anatomical parameter. For example, the interface unit 12 may be configured to output or export derived physiological or anatomical parameter measurements to a cloud storage server or platform.

In some examples, the deriving the one or more anatomical or physiological parameters is based on use of one or more machine learning algorithms or models. The interface unit 12 may be configured to export derived parameters measurements to a remote server for archiving, e.g. a cloud server. There may further be provided an algorithm training facility, wherein training of the one or more machine learning algorithms is performed based on the archived parameter measurement results. Updated algorithms or models may be communicated to the interface unit 12, and applied by the interface unit for future parameter derivation. Such algorithm or model training may be performed on a patient-specific basis, so that for each patient, the algorithm is trained and updated based on results of the patient's own measurements, such that a dedicated algorithm is developed for each patient.

There are different options for the physical configuration of the ultrasound interface unit 12. Various options will now be outlined. Any of the features, functions and options discussed above may be applied to any one of the different embodiments discussed below.

In accordance with one set of embodiments, the ultrasound interface unit 12 is provided as a separate stand-alone unit which has connection ports for connecting in use with each of an ultrasound sensing apparatus 14 and a patient monitoring unit 18. It hence provides a bridge between an ultrasound sensing apparatus 14 and a patient monitoring unit 18, effectively adding additional processing capability to the patient monitor, to allow for deriving and monitoring physiological or anatomical parameters based on the ultrasound data. Hence, it allows the patient monitor to effectively use the existing ultrasound sensing apparatus as an additional patient monitoring input, in addition to other medical sensors that may be coupled to the patient monitor.

The ultrasound interface unit may in this case provide a retrofit capability, allowing any existing patient monitoring unit 18 and ultrasound sensing apparatus 14 to be hooked up together, and used, by means of the interface unit 12, for implementing ultrasound monitoring of the relevant parameters.

The interface unit 12 may be configured to be connected with the ultrasound sensing apparatus 14 via a wired or wireless connection. The interface unit may include a wired or wireless connection port for facilitating this connection. The ultrasound apparatus may stream ultrasound data to the interface unit. The ultrasound data may include for example ultrasound images or volumes. The ultrasound apparatus may have means for locally deriving one or more measurements from acquired ultrasound data. Optionally in this case, the interface unit may be configured to further receive from the ultrasound apparatus one or more such measurements computed by the US apparatus).

The interface unit 12 is configured to connect via wired or wireless connection to the patient monitoring unit. It may be configured to connect via institutional wireless LAN in some examples. The interface unit may include a wired or wireless connection port for facilitating this. The interface unit is configured to communicate physiological and/or anatomical parameter measurements derived by the interface unit. These may be displayed on the patient monitor screen and/or stored or cached at the patient monitor. They may be trended on the patient monitor's display, i.e. showing changes in the parameter over time.

There are different options for the ultrasound sensing apparatus 14.

Figure 3:
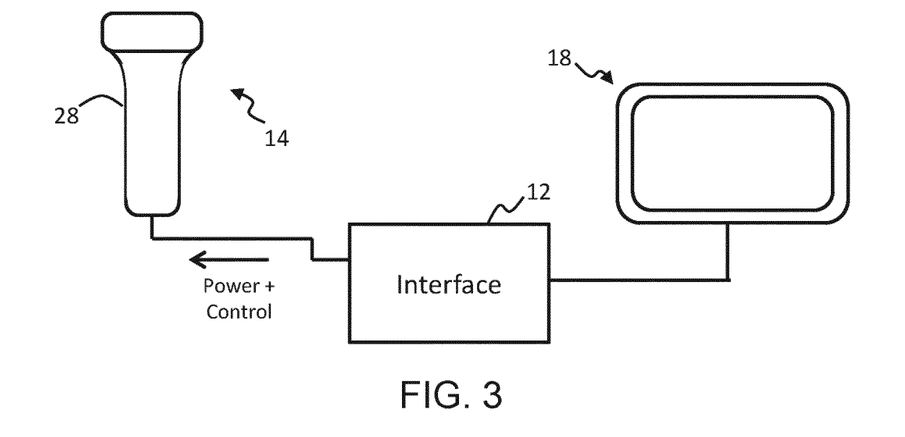
FIG. 3 schematically shows an example ultrasound interface unit in use, coupled to a standalone ultrasound transducer unit.

One example is shown in FIG. 3. In this example, the ultrasound sensing apparatus 14 comprises a standalone ultrasound transducer unit 28 or sensor, e.g. a standalone probe, not comprising associated transducer drive means or signal processing means.

In this case, the ultrasound interface unit 12 may be configured to provide a power supply to the ultrasound apparatus for use in powering driving of the ultrasound transducers. The interface unit hence acts as a power source for the ultrasound apparatus.

In advantageous examples, the ultrasound interface unit may generate and output drive signals for driving the ultrasound transducers of the ultrasound transducer unit 28. The drive signals directly power vibration of the transducers. They hence carry power for driving the transducers, but also directly control signal transmission. Hence, the interface provides both power to and control of the ultrasound sensing apparatus transducers.

Hence, in this set of examples, the configuration function performed by the interface unit 12 may comprise configuring parameters of these generated drive signals.

In this case, the interface unit 12 may be configured to receive RF ultrasound data. The interface unit may be configured to perform processing of this data to derive post-processed data (e.g. scan-converted data and/or ultrasound images). Hence, the interface unit may play the role of an ultrasound processing unit or image formation processor.

By way of example, the standalone ultrasound transducer unit 28 may comprise a USB ultrasound probe, designed for connecting to an ultrasound system via a USB connection. This probe can be utilized by the interface unit to acquire suitable ultrasound data for monitoring the one or more physiological parameters, and outputting these to the patient monitoring unit 18. The USB probe may be plugged directly into a suitable connector socket on the interface unit 12 for example. Although USB is mentioned, the ultrasound probe may instead connect via any connection means, wired or wireless, using any communication or communication standard (e.g. Ethernet, serial, parallel or any other).

Although not shown in FIG. 3, preferably, the interface unit further comprises a coupled display unit 24. Preferably, where the connected ultrasound sensing apparatus is a standalone ultrasound transducer unit 28, this display unit can be used to display real-time ultrasound data, e.g. generated ultrasound image data, for assisting a user in positioning and operating the ultrasound transducer unit. The display unit hence effectively acts as a primary ultrasound display as might be found on a broader ultrasound diagnostic system. The optional display may be controlled to display US data, and/or to display results of the at least one monitored physiological or anatomical parameter. The display may be switched intermittently between these two, or the measurement results may in some examples be displayed overlaid atop generated ultrasound images (as discussed above).

Figure 4:
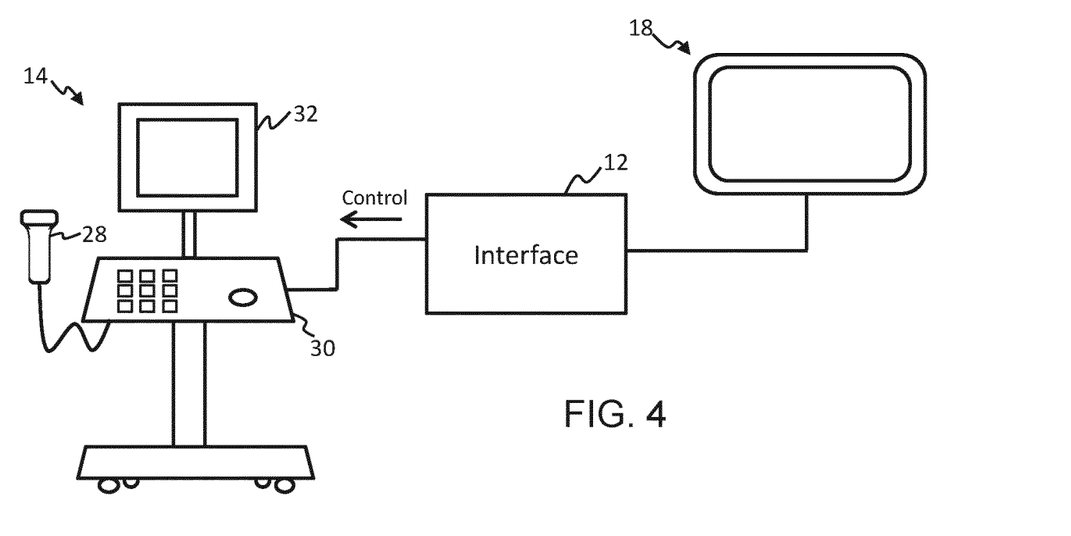
FIG. 4 schematically shows an example ultrasound interface unit in use, coupled to an ultrasound system having ultrasound data processing means.

A further example is shown in FIG. 4.

In this example, the coupled ultrasound sensing apparatus 14 may be an ultrasound system comprising one or more ultrasound transducer units 28, and further comprising local drive means 30 for generating drive signals for driving ultrasound transmission by transducers of the one or more ultrasound transducer units 28. In this case, the configuring function comprises communicating with the ultrasound sensing apparatus to cause the ultrasound sensing apparatus to adjust parameters of said locally generated drive signals.

Hence, in this case, the ultrasound interface unit 12 need not provide a power supply to the ultrasound sensing apparatus 14, and need not generate drive signals for driving the ultrasound transducers of the ultrasound sensing apparatus 14. The interface unit may generate control signals or commands for causing the processing means 30 of the ultrasound sensing apparatus to adjust the operating parameters of the signal transmission, e.g. frequency, signal strength, beam-steering direction, or any other parameter.

The processing means 30 of the ultrasound sensing apparatus 14 may comprise means for post-processing RF ultrasound data received from the one or more ultrasound transducer units 28, for example for performing receive beamforming, and/or for scan converting the data to generate image data.

The processing means 30 may be configured to process ultrasound data received from the at least one transducer unit 30 to generate one or more ultrasound images.

The ultrasound apparatus 14 may include a local display unit 32 for displaying a representation of received ultrasound data, for example for displaying one or more generated ultrasound images.

The ultrasound apparatus may comprise a user input means for permitting entry by a user of user input commands, for controlling operating parameters of the ultrasound acquisition, and/or for labelling acquired ultrasound data.

In FIG. 4, the processing unit 30 also performs the function of the local drive means for supplying drive signals to the ultrasound transducers. However, this is not essential. There may be a separate processing unit, with which the interface unit communicates, and a separate drive means, communicatively coupled with the control unit, and adapted to generate the drive signals for driving the ultrasound transducers.

The interface unit may be adapted to transmit control commands to a control unit of the ultrasound sensing apparatus in the form of one or more data signals or data messages. The control unit of the ultrasound sensing apparatus may communicate with a local drive means to cause adjustment in the ultrasound acquisition parameters (e.g. transmit/receive signals) based on the received data signals or data messages. The data messages or signals may include instructions or requests indicative of a required change to one or more properties of the ultrasound data acquisition. These may relate to properties of the ultrasound data being acquired, such as the ultrasound field of view, or the depth level of the ultrasound data, or the data acquisition mode (e.g. 2D/3D, B-mode, C-mode), or may relate to properties of the drive scheme being used by the local drive means to drive the ultrasound transducers.

In accordance with one possible set of embodiments, the interface unit may be selectively operable in either of two modes:

a first mode in which the interface unit is configured in use to supply power to the ultrasound sensing apparatus for driving ultrasound transmission by ultrasound transducers of the ultrasound sensing apparatus, and a second mode in which the ultrasound interface unit is adapted to be communicatively coupleable with an ultrasound sensing apparatus which includes local drive means for generating drive signals for driving ultrasound transmission by transducers of the ultrasound sensing apparatus, and wherein the configuring function comprises communicating with the ultrasound sensing apparatus to cause the ultrasound sensing apparatus to adjust parameters of said locally generated drive signals.

Depending upon which type of ultrasound apparatus is connected to the interface unit, the appropriate mode can be selected. The mode may be selected automatically by a controller of the interface unit, or it may be user-selected in some examples, using a user interface.

The ultrasound apparatus may take the form of a trolley cart mounted on casters or wheels, the cart carrying the processing means 30, and the optional display 32.

Figure 5:
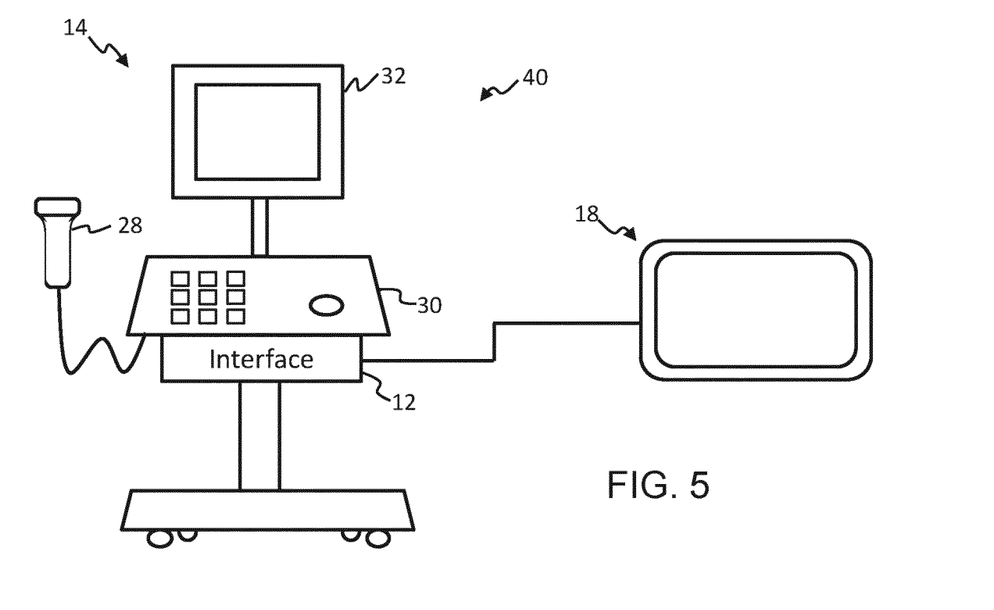
FIG. 5 shows an ultrasound system comprising an ultrasound interface unit integrated with an ultrasound sensing apparatus.

FIG. 5 shows a further embodiment. Here, an ultrasound system 40 is provided comprising an ultrasound sensing apparatus 14, for example in accordance with any of the examples discussed above, and an ultrasound interface unit 12 in accordance with any example or embodiment outlined above or described below, or in accordance with any claim of this application.

The ultrasound interface unit 12 in this set of embodiments is provided integrated as a component of the ultrasound sensing apparatus 14. However, this is just one option and is not essential; the two units may be provided physically separate.

In examples, the ultrasound apparatus may comprise a base station, and wherein the interface unit 12 is integrated with at least a portion of the base station, for example coupled to the base station.

In the particular example of FIG. 5, the ultrasound sensing apparatus 14 comprises a trolley-type ultrasound system as discussed above, comprising an ultrasound processing means 30 and a coupled one or more ultrasound transducer units 28 or sensors. The ultrasound apparatus 14 optionally further includes a display unit 32. However, this represents just one example, and the ultrasound apparatus may in other examples take a different structural configuration.

In the example of FIG. 5, the ultrasound interface unit 12 is provided coupled to the processing means 30 of the ultrasound sensing apparatus 14. In other examples, the interface unit may be provided integrated inside a common outer housing along with the processing means. In further examples, the interface unit may be provided as a removable module within the ultrasound apparatus, for instance slotted into a receiving slot.

The processing means 30 and the interface unit 12 may be coupled via an external wired or wireless connection (e.g. LAN, HDMI, USB or other), or may be coupled for instance via hidden integrated internal wiring.

In some examples, the display unit 32 of the ultrasound sensing apparatus 14 may be used for displaying the results of the one or more physiological or anatomical parameters derived by the interface unit 12. Switching may be implemented between a conventional US display (displaying generated ultrasound images) and a monitoring display (displaying physiological or anatomical parameters derived from the ultrasound data).

In some examples, a secondary display (not shown) may be provided communicatively coupled with the interface unit 12 and wherein the interface unit controls this secondary display to display results of the one or more physiological or anatomical parameters derived by the interface unit. This may be alternative to, or in addition to, showing the results on the patient monitoring unit 18 display.

In some examples, the interface unit 12 is not integrated in the ultrasound apparatus 14 but provided spatially separated from it. A secondary display may be provided physically mounted to the ultrasound apparatus 14, communicatively coupled with the interface unit 12 for displaying the results of the one or more physiological or anatomical parameters derived by the interface unit 12. The secondary display may for instance be implemented as an additional display adjacent the primary display 32 of the ultrasound apparatus (where such a primary display is included as part of the apparatus). The secondary display may be a swivelable display for example.

The interface unit 12 of the system 40 further comprises a connection port for connecting in use with a patient monitor 18. This may be a wired or wireless connection port for making wired or wireless connection. This connection allows measurements derived by the interface unit to be communicated to the patient monitoring unit 18 and trended on the patient monitor's display.

Figure 6:
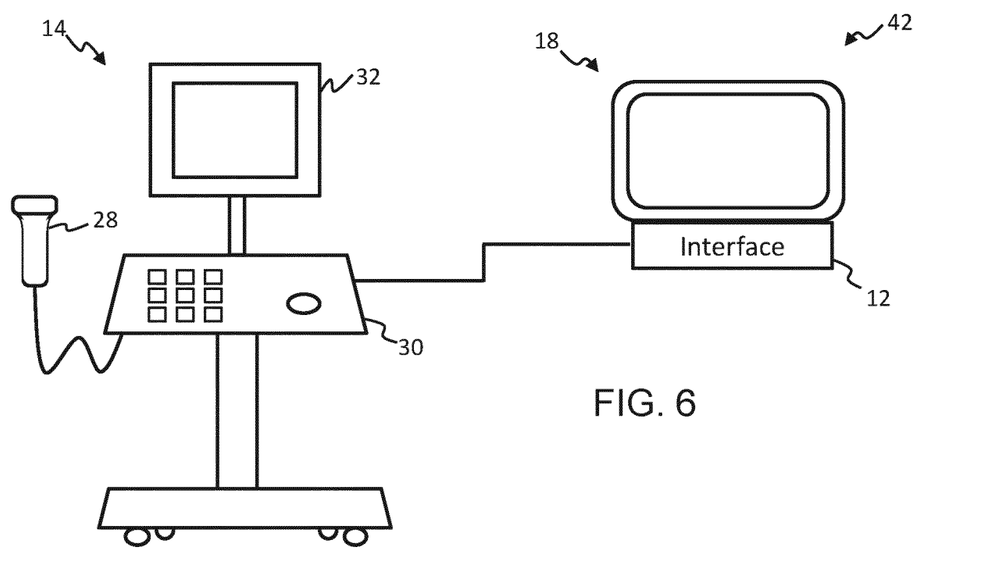
FIG. 6 shows a further example ultrasound system comprising an ultrasound interface unit integrated with a patient monitoring unit.

FIG. 6 shows an example in accordance with a further embodiment.

This set of embodiments comprises an ultrasound system 42 comprising a patient monitoring unit 18 being communicatively coupleable with one or more medical sensors for receiving medical sensor data, and an ultrasound interface unit 12 in accordance with any example or embodiment outlined above or described below, or in accordance with any claim of this application.

In the example illustrated, the ultrasound interface unit 12 is integrated as part of the patient monitoring unit 18. However, this is just one option and is not essential. In other examples, the two units may be provided physically separate.

In some examples, the patient monitoring unit may comprise a base station, and the interface unit may be integrated within a housing of the base station.

The patient monitoring unit comprises a display for displaying sensor data received from one or more medical sensors coupleable in use with the patient monitoring unit 18. In the illustrated example, the patient monitoring unit comprises a small tablet-type device. However, in other examples, the patient monitor may comprise a larger trolley-type configuration comprising a base station mounted on a trolley cart having casters or wheels to permit wheeled ambulation of the cart. The patient monitor may comprise a display and may comprise a user input means.

In either case, the medical sensors may be coupled to the patient monitor either through wired or wireless connection.

The interface unit 12 is coupled to the patient monitor via any suitable wired or wireless connection. This may be an external connection, or through hidden integrated internal wiring for instance.

The interface unit 12 is coupleable in use with an ultrasound sensing apparatus 14 for receiving ultrasound data from the apparatus. As discussed above, the ultrasound data may include ultrasound data at any point along a series of post-processing operations. The ultrasound data may include generated ultrasound images in some examples. The ultrasound apparatus may in some examples be configured to derive one or more measurements locally at the apparatus, and may communicate these measurements to the interface unit 12.

In preferred examples, a secondary display unit (not shown) is provided coupled to the interface unit, and wherein the interface unit is configured to control the display unit to display results of the one or more derived physiological measurements (as discussed above). By way of example, the results may be displayed overlaid atop generated ultrasound images. For example, segmented maps of one or more anatomical bodies may be shown overlaid atop ultrasound images of the relevant anatomical regions.

In some examples, the interface unit 12 is not integrated in the patient monitoring unit 18 but provided spatially separated from it. A secondary display may be provided physically mounted to the patient monitoring unit, communicatively coupled with the interface unit 12 for displaying the results of the one or more physiological or anatomical parameters derived by the interface unit 12. The secondary display may for instance be implemented as an additional display adjacent a primary display of the patient monitoring unit. The secondary display may be a swivelable display for example.

Examples in accordance with a further aspect of the invention provide an ultrasound interface method, comprising receiving from an ultrasound sensing apparatus acquired ultrasound data representative of a subject, and performing processing of said data to derive at least one physiological or anatomical parameter related to the subject;

generating a data output representative of said derived parameter and communicating said data output to a patient monitoring unit, and performing a configuration function comprising communicating with the ultrasound sensing apparatus to cause adjustment of one or more operating parameters of the ultrasound sensing apparatus for configuring the ultrasound sensing apparatus to acquire ultrasound data suitable for monitoring said physiological or anatomical parameter.

According to one or more embodiments, the method may further comprise generating guidance information for guiding a user in positioning an ultrasound transducer unit of the ultrasound sensing apparatus relative to the subject for acquiring ultrasound data suitable for determining said at least one physiological or anatomical parameter; and generating a display output for use in controlling a display unit to display said guidance information for adjustment of the ultrasound transducer unit position.

Implementation options and details for each of the above steps may be understood and interpreted in accordance with the explanations and descriptions provided above for the apparatus aspect of the present invention (i.e. the ultrasound interface aspect).

Any of the examples, options or embodiment features or details described above in respect of the apparatus aspect of this invention (in respect of the interface unit) may be applied or combined or incorporated into the present method aspect of the invention.

Examples in accordance with a further aspect of the invention also provide a computer program product comprising code means configured, when run on a processor, to cause the processor to perform the method outlined above.

As discussed above, various embodiments make use of one or more processors or processing means to perform the data processing. The processors or processing means can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An ultrasound interface unit, communicatively coupleable in use with both: an ultrasound sensing apparatus and a patient monitoring unit, said ultrasound interface unit configured in use to:
receive from the ultrasound sensing apparatus acquired ultrasound data representative of a subject, and perform processing of said data to derive at least one physiological or anatomical parameter related to the subject;
generate a data output representative of said derived parameter and communicate said data output to the patient monitoring unit, and
perform a configuration function comprising communicating with the ultrasound sensing apparatus to cause adjustment of one or more operating parameters of the ultrasound sensing apparatus for configuring the ultrasound sensing apparatus to acquire ultrasound data suitable for monitoring said physiological or anatomical parameter over time,
wherein the interface unit is further configured to generate guidance information for guiding a user in positioning an ultrasound transducer unit of the ultrasound sensing apparatus relative to the subject for acquiring ultrasound data suitable for determining said at least one physiological or anatomical parameter, and wherein the interface unit is configured to generate a display output for use in controlling a display unit to display said guidance information for adjustment of the ultrasound transducer unit position.

2. The ultrasound interface unit of claim 1, wherein the ultrasound interface unit is configured in use to supply power to the ultrasound sensing apparatus for driving ultrasound transmission by ultrasound transducers of the ultrasound sensing apparatus.

3. The ultrasound interface unit of claim 1, wherein the ultrasound sensing apparatus is an ultrasound transducer unit comprising one or more ultrasound transducers.

4. The ultrasound interface unit of claim 3, wherein the interface unit is configured to generate drive signals for driving ultrasound transmission by the ultrasound transducers of the ultrasound transducer unit, wherein the configuration function comprises configuring parameters of said drive signals.

5. The ultrasound interface unit of claim 1, wherein the ultrasound sensing apparatus includes local drive means for generating drive signals for driving ultrasound transmission by transducers comprised by an ultrasound transducer unit of the ultrasound sensing apparatus, and wherein the configuration function comprises communicating with the ultrasound sensing apparatus to cause the ultrasound sensing apparatus to adjust parameters of said locally generated drive signals.

6. The ultrasound interface unit of claim 1, wherein the ultrasound interface unit further comprises a display unit for displaying the at least one derived anatomical or physiological parameter and/or for displaying one or more ultrasound images generated based on the acquired ultrasound data.

7. The ultrasound interface unit of claim 1, wherein the ultrasound sensing apparatus comprises a display unit and the ultrasound interface unit is adapted to communicate said display output to the ultrasound sensing apparatus for causing display of the guidance information on the display unit of the ultrasound sensing apparatus.

8. The ultrasound interface unit of claim 1, wherein the ultrasound sensing apparatus comprises a display unit, and the ultrasound interface unit is configured to communicate with the ultrasound sensing apparatus to cause display on said display unit of the at least one physiological or anatomical parameter derived by the interface unit.

9. The ultrasound interface unit of any of claim 1, wherein the ultrasound data received from the ultrasound sensing apparatus includes ultrasound image data.

10. The ultrasound interface unit of claim 1, wherein the ultrasound interface unit is adapted to receive an input signal from the patient monitoring unit and is adapted to perform the configuring of the operating parameters of the ultrasound sensing apparatus based on the input signal.

11. The ultrasound interface unit of claim 1, wherein the ultrasound interface unit is further coupleable in use with one or more medical sensors for measuring one or more physiological parameters and the interface unit configured to receive sensor data from said one or more sensors.

12. An ultrasound system, comprising:
an ultrasound sensing apparatus, and
an ultrasound interface unit in accordance with claim 1, communicatively coupled with the ultrasound sensing apparatus.

13. The ultrasound system of claim 1, wherein the ultrasound sensing apparatus comprises a base station comprising processing means for processing ultrasound data acquired by one or more ultrasound transducers to generate one or more ultrasound images, and wherein the ultrasound interface unit is integrated within the base station.

14. An ultrasound system, comprising:
a patient monitoring unit being communicatively coupleable with one or more medical sensors for receiving medical sensor data, and
an ultrasound interface unit in accordance with claim 1, communicatively coupled with the patient monitoring unit.

15. The ultrasound system of claim 14, wherein the patient monitoring unit comprises a base station comprising processing means arranged to receive the medical sensor data, and wherein the ultrasound interface unit is integrated within said base station.

16. An ultrasound interface method, comprising:
receiving from an ultrasound sensing apparatus acquired ultrasound data representative of a subject, and performing processing of said data to derive at least one physiological or anatomical parameter related to the subject;
generating a data output representative of said derived parameter and communicating said data output to a patient monitoring unit;
performing a configuration function comprising communicating with the ultrasound sensing apparatus to cause adjustment of one or more operating parameters of the ultrasound sensing apparatus for configuring the ultrasound sensing apparatus to acquire ultrasound data suitable for monitoring said physiological or anatomical parameter;
generating guidance information for guiding a user in positioning an ultrasound transducer unit of the ultrasound sensing apparatus relative to the subject for acquiring ultrasound data suitable for determining said at least one physiological or anatomical parameter; and
generating a display output for use in controlling a display unit to display said guidance information for adjustment of the ultrasound transducer unit position.

17. A computer program product comprising code means configured, when run on a processor, to cause the processor to perform the method of claim 16.

* * * * *